United States Patent [19]

Clitherow

[11] 4,413,135
[45] Nov. 1, 1983

[54] INTERMEDIATES IN THE PREPARATION OF RANITIDINE

[75] Inventor: John W. Clitherow, Hertfordshire, England

[73] Assignee: Glaxo Group Limited, London, England

[21] Appl. No.: 385,075

[22] Filed: Jun. 4, 1982

Related U.S. Application Data

[62] Division of Ser. No. 223,484, Jan. 8, 1981, abandoned.

[30] Foreign Application Priority Data

Jan. 8, 1980 [GB] United Kingdom ............... 8000581
Aug. 12, 1980 [GB] United Kingdom ............... 8038336

[51] Int. Cl.³ .................. C07D 307/52; C07D 307/54
[52] U.S. Cl. ............................................. 549/495
[58] Field of Search ......................................... 549/495

[56] References Cited

U.S. PATENT DOCUMENTS 4,255,440 3/1981 Price et al. ..................... 549/495 X

FOREIGN PATENT DOCUMENTS 2075980 11/1981 United Kingdom .

*Primary Examiner*—Richard Raymond
*Attorney, Agent, or Firm*—Bacon & Thomas

[57] ABSTRACT

The invention relates to a process for the preparation of ranitidine of formula (I)

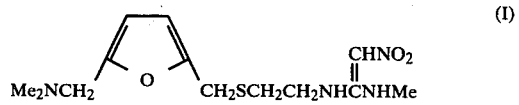

which comprises reacting a thiol of formula (II)

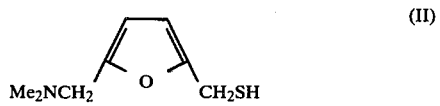

with an alkylating agent of formula (III)

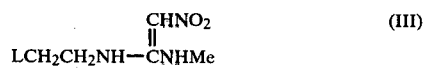

where L is a leaving group, preferably halogen.

The invention also relates to novel intermediates, the thiol of formula (II)

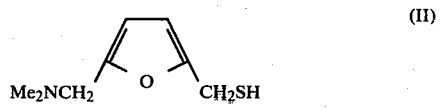

in the form of a stable acid addition salt, and the isothiourea of formula (IV)

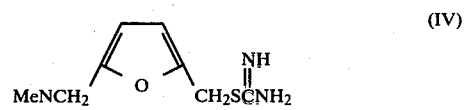

and stable acid additions salts thereof.

2 Claims, No Drawings

INTERMEDIATES IN THE PREPARATION OF RANITIDINE

This application is a division, of application Ser. No. 223,484, filed Jan. 8, 1981, now abandoned.

This invention relates to a process for the preparation of a furan derivative.

The furan derivative of formula (I)

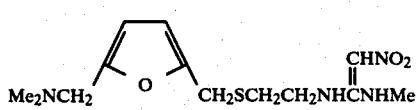

which is known as ranitidine is disclosed in British Patent No. 1,565,966 as a potent and selective $H_2$-antagonist.

The present invention provides a process for the preparation of the furan derivative of formula (I) which comprises reacting a thiol of formula (II)

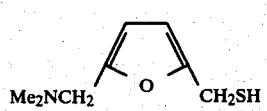

with an alkylating agent of formula (III)

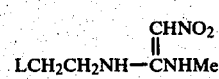

where L is a leaving group.

An example of a suitable leaving group L is a halogen atom, chlorine being preferred.

The process of the present invention provides a novel and useful method for the preparation of the compound ranitidine.

The process according to the invention may be carried out in a suitable solvent such as water, aqueous tetrahydrofuran, dimethylformamide, an alkanol (e.g. methanol) or a ketonic solvent such as acetone optionally with the addition of water. The reaction is preferably carried out in the presence of a base such as an inorganic base (e.g. an alkali metal carbonate or hydroxide such as potassium carbonate or potassium or sodium hydroxide), an alkoxide (e.g. sodium methoxide) or a tertiary amine (e.g. triethylamine), and at a suitable temperature for example within the range of 10° to 80° C. The reaction is preferably effected in an inert atmosphere, for example under nitrogen. In a modification of this process the thiol of formula (II) may be reacted with the alkylating agent (III) in a two phase system using for example chloroform and water, in the presence of a phase transfer catalyst (e.g. a quaternary ammonium salt such as benzyltriethylammonium chloride) and a base (e.g. sodium hydroxide).

Particularly advantageous conditions for carrying out the alkylation reaction include treating the thiol of formula (II) with the alkylating reagent (III) (in which L is chlorine) either in the presence of an alkali metal hydroxide (e.g. potassium hydroxide) in water, or in the presence of potassium carbonate using aqueous tetrahydrofuran as the solvent. Advantageously the reaction is carried out at room temperature under an atmosphere of nitrogen.

The thiol (II) may be used directly or is generated in situ from an acid addition salt such as an oxalate salt. Alternatively, when the reaction is carried out in the presence of a base, the thiol (II) may be generated in situ from the isothiourea (IV) or a salt thereof, for example a bis maleate salt, under the basic conditions of the reaction.

The thiol of formula (II) may be prepared by reacting the corresponding alcohol of formula (V)

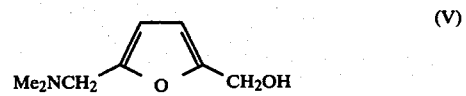

with thiourea in the presence of a concentrated acid such as concentrated hydrochloric acid to produce the isothiourea (IV), which is then converted into the thiol of formula (II) by treatment with a base such as sodium carbonate or 5 N sodium hydroxide, preferably in the presence of an antioxidant such as sodium dithionite or or sodium metabisulphite. Once isolated, the free base thus formed may be converted into a stable acid addition salt by treatment with an appropriate acid, in particular oxalic acid, preferably in a solvent such as tetrahydrofuran.

If it is desired to isolate the isothiourea (IV) this is also preferably isolated in the form of a stable salt, e.g. the bis-maleate, by treatment with an appropriate acid preferably in a solvent such as tetrahydrofuran.

The compound of formula (III) in which L is halogen (e.g. chlorine) may be prepared by reacting a compound of formula (VI)

(in which L' is a leaving group e.g. methylthio) with a haloalkylamine such as chloroethylamine preferably in the form of a salt e.g. a hydrochloride. The reaction is carried out in a suitable solvent such as water, in the presence of a base such as triethylamine, and preferably at an elevated temperature, for example at about 100° C.

The acid addition salts of the thiol of formula (II), and the isothiourea of formula (IV) and acid addition salts thereof are all novel compounds and should be regarded as part of the present invention.

The thiol of formula (II) and the isothiourea of formula (IV) are not particularly stable but it has been found that they can be stabilised by converting them into the form of an acid addition salt. Examples of such stable acid addition salts include hydrochlorides, sulphates, alkyl and aryl sulphonates, acetates, fumarates, maleates and benzoates. A preferred acid addition salt of the thiol of formula (II) is an oxalate, and a preferred acid addition salt of the isothiourea (IV) is the bis maleate.

The invention is illustrated by the following Examples.

PREPARATION 1

1-[[[5-[(Dimethylamino)methyl]-2-furanyl]methyl]thio]methanimidamide, maleate (1:2)

5-[(Dimethylamino)methyl]-2-furanmethanol (3.1 g) was added gradually to a solution of thiourea (1.53 g) in concentrated hydrochloric acid (5 ml). After standing at room temperature for 18 h, the solution was heated at 98°–100° for 30 minutes. The solution was cooled, tetrahydrofuran (100 ml) and an excess of anhydrous sodium carbonate added and after 30 minutes the mixture was filtered. A solution of maleic acid (4.65 g) in dry tetrahydrofuran (40 ml) was added to the filtrate and the solid which separated was filtered, washed with tetrahydrofuran and ether to give the title compound (8.1 g) m.p. 144°–145°.

PREPARATION 2

5-[(Dimethylamino)methyl]-2-furanmethanethiol, oxalate (1:1)

5-[(Dimethylamino)methyl]-2-furanmethanol (7.76 g) was added gradually to a solution of thiourea (3.81 g) in concentrated hydrochloric acid (12.5 ml). After 18 h, the solution was heated for 30 minutes at 98°–100° and evaporated to low bulk. A solution of sodium hydroxide (10 g) in water (50 ml) and sodium dithionite (10 g) was added and after 1 h the solution was extracted with ether (6×50 ml). Boric acid (35 g) was added to the aqueous fraction and the suspension was extracted with ether (4×50 ml). To the combined ethereal extracts was added sodium dithionite (2 g) and an excess of anhydrous sodium carbonate. After 3 h, the mixture was filtered into a solution of oxalic acid (6.3 g) in dry tetrahydrofuran (60 ml).

The solid which separated was filtered, washed with tetrahydrofuran and dried to give the title compound (5.84 g), m.p. 116.5°–118°.

PREPARATION 3

N-(2-Chloroethyl)-N'-methyl-2-nitro-1,1-ethenediamine

To a solution of N-methyl-(1-methylthio)-2-nitroethenamine (5.93 g) and 2-chloroethanamine hydrochloride (18.56 g) in water (4 ml) at 98°–100° was added triethylamine (24 ml). The mixture was stirred at 98°–100° for 10 mins and a vacuum (12 to 20 mm) applied for 50 mins. Water (8 ml) was added and the mixture heated in vacuo at 98°–100° for 20 mins. Acetone (200 ml) and an excess of anhydrous magnesium sulphate were added to the residue and the suspension refluxed for 45 mins. The solid was filtered off and washed with hot acetone (3×50 ml). The combined filtrate and washings were cooled and the resulting crystalline precipitate separated by filtration. The filtrate was concentrated to 100 ml, the solid which separated was filtered off, and the filtrate evaporated to low bulk and chromatographed (silica/acetone). The appropriate eluate was evaporated in vacuo, the residue suspended in ethyl acetate:ether, 1:4 and filtered to give the title compound (2.8 g) m.p. 113°–115°. T.l.c. silica;2-butanone; $R_f$ 0.4.

PREPARATION 4

5-[Dimethylamino)methyl]-2-furanmethanethiol oxalate (1:1)

A mixture of potassium carbonate (83.5 g), sodium metabisulphite (22.9 g) and 1-[[[5-[(dimethylamino)methyl]-2-furanyl]methyl]thio]methanimidamide maleate (1:2) (26.73 g) in water (140 ml) and ether (160 ml) was stirred under a nitrogen atmosphere at room temperature for 24 h. Anhydrous sodium carbonate (10 g) was added and after stirring for a further 2 h, the ether fraction was separated and washed with a solution of sodium metabisulphite (5 g) and potassium carbonate (8 g) in water (60 ml). The ether extract was dried ($Na_2SO_4$) for 1 h and filtered into a solution of oxalic acid (7.6 g) in tetrahydrofuran (100 ml). The solid which separated (13.33 g) was crystallised from tetrahydrofuran to give the title compound (12.20 g), m.p. 116.5°–119°.

EXAMPLE 1

N-[2-[[5-[(Dimethylamino)methyl]-2-furanylmethyl]thio]ethyl]-N'-methyl-2-nitro-1,1-ethenediamine A mixture of N-(2-chloroethyl)-N'-methyl-2-nitro-1,1-ethenediamine (0.9 g), 5-[(dimethylamino)methyl]-2-furanmethanethiol oxalate (1:1) (1.3 g) and potassium carbonate (2.7 g) in water (10 ml) and tetrahydrofuran (10 ml) was stirred under nitrogen at room temperature for 5 days. The suspension was evaporated in vacuo, the residue mixed with water (40 ml) and the suspension extracted with ether (2×30 ml). The aqueous fraction was evaporated in vacuo and the residue evaporated with ethanol (2×10 ml). Tetrahydrofuran (20 ml), $MgSO_4$ and decolourising charcoal were added and after 1 hour the mixture was filtered. Evaporation of the filtrate gave an oil (1 g) which was chromatographed (silica/methanol: 0.88 ammonia, 79:1). The appropriate eluate was evaporated and the oily residue (0.66 g) extracted with hot isopropyl acetate. The solid which separated was filtered to give the title compound (0.4 g), m.p. 65°–68°, which was not depressed on admixture with a sample prepared according to the method of Example 15 in British Patent No. 1,565,966.

EXAMPLE 2

N-[2-[[5-[(Dimethylamino)methyl]-2-furanylmethyl]thio]ethyl]-N'-methyl-2-nitro-1,1-ethenediamine A mixture of 1-[[[5-[(dimethylamino)methyl]-2-furanyl]-methyl]thio]methanimidamide maleate (1:2) (2.23 g), N-(2-chloroethyl)-N'-methyl-2-nitro-1,1-ethenediamine (0.9 g) and potassium carbonate (3.46 g) in water (10 ml) and tetrahydrofuran (10 ml) was stirred under nitrogen at room temperature for 5 days. The suspension was evaporated in vacuo; the residue suspended in water (50 ml) and extracted with ether (2×40 ml). The aqueous fraction was evaporated in vacuo and magnesium sulphate and tetrahhydrofuran (100 ml) added. After 18 hours, the mixture was filtered and the filtrate evaporated to give a semi-solid which was chromatographed (silica/methanol). The appropriate eluate was evaporated in vacuo to give the title compound (0.3 g), which had an n.m.r. identical to that of the product according to Example 1 above.

EXAMPLE 3

N-[2-[[5-[(Dimethylamino)methyl]-2-furanylmethyl]thio]ethyl]-N'-methyl-2-nitro-1,1-ethenediamine To a stirred mixture of 5-[(dimethylamino)methyl]-2-furanmethane-thiol oxalate (1:1) (1.31 g) and N-(2-chloroethyl)-N'-methyl-2-nitro-1,1-ethenediamine (1.08 g) in water (20 ml) at 45° under an atmosphere of nitrogen was added a solution of potassium hydroxide (1.04 g) in water (3 ml). The solution was stirred at 45° for 2.5 hr. and at room temperature for 15 hr. The solution was then evaporated in vacuo, the residue dissolved in water and a stream of air passed into the mixture for 15 mins. The mixture was extracted with ether (2×15 ml) and the aqueous fraction evaporated in vacuo. To the residue was added tetrahydrofuran (70 ml), an excess of anhydrous sodium carbonate, and decolourising charcoal. After 1 hr the mixture was filtered, the filtrate evaporated in vacuo and the oily residue dissolved in 4-methyl-pentan-2-one (8 ml). The solid which separated was filtered and washed with 4-methylpentan-2-one to give the title compound (0.72 g), m.p. 63°–66°, which was not depressed on admixture with a sample prepared according to the method of Example 15 in British Patent No. 1,565,966.

EXAMPLE 4

N-[2-[[5-[(Dimethylamino)methyl]-2-furanylmethyl]thio]ethyl]-N'-methyl-2-nitro-1,1-ethenediamine To a stirred solution of 1-[[5-[(Dimethylamino)methyl]-2-furanylmethyl]thio]methanimidamide maleate (1:2) (2.23 g) and N-(2-chloroethyl)-N'-methyl-2-nitro-1,1-ethenediamine (1.08 g) in water (20 ml) at 45° under an atmosphere of nitrogen was added a solution of potassium hydroxide (1.68 g) in water (3 ml). After 40 hr. at room temperature the solution was extracted with ether (2×50 ml) and the aqueous phase evaporated in vacuo. Tetrahydrofuran (70 ml), decolourising charcoal and an excess of anhydrous sodium carbonate were added to the residue and the mixture refluxed for 30 mins. After 3 hours the mixture was filtered and the filtrate evaporated in vacuo to give a semi-solid which was dissolved in a mixture of methanol and acetone and chromatographed (silica;methanol:acetone 1:1). The appropriate eluate was evaporated in vacuo to give the title compound as an oil (0.37 g), a portion of which was crystallised from 4-methylpentan-2-one, m.p. 68°–70° which was not depressed on admixture with a sample prepared according to the method of Example 15 in British Patent No. 1,565,966.

I claim:

1. The thiol of formula (II)

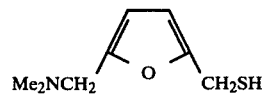

(II)

in the form of a stable acid addition salt.

2. The isothiourea of formula (IV)

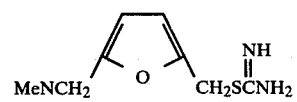

(IV)

and stable acid addition salts thereof.

* * * * *